United States Patent [19]

Ho et al.

[11] 4,393,130

[45] Jul. 12, 1983

[54] SYSTEM FOR ENCAPSULATION OF SEMICONDUCTOR CHIPS

[75] Inventors: Nelson Ho, West Valley; Jiri Kratochvil, Sandy, both of Utah

[73] Assignee: Critikon, Inc., Tampa, Fla.

[21] Appl. No.: 338,732

[22] Filed: Jan. 11, 1982

[51] Int. Cl.³ .............................................. G03C 5/00
[52] U.S. Cl. .................................... 430/313; 430/321; 430/324
[58] Field of Search ....................... 430/313, 321, 324; 357/25

[56] References Cited

U.S. PATENT DOCUMENTS 3,832,176 8/1974 Verstraete et al. ................. 430/324
4,020,830 5/1977 Johnson et al. ..................... 128/2 E Primary Examiner—John E. Kittle
Assistant Examiner—José G. Dees
Attorney, Agent, or Firm—Audley A. Ciamporcero, Jr.

[57] ABSTRACT

A system for encapsulating semiconductor chips, such as chips carrying chemical sensitive field-effect devices, includes lamination of a sheet of dry film photoresist material onto the surface of the chip, placement of a photomask over the chip in a predetermined alignment, and then exposure of the photomask to light so that light passes through certain light-transmitting portions of the mask onto the chip. The photoresist material is then developed to remove the material from over the gate regions of each of the field-effect devices to define windows in the material through which the gate regions are exposed. Chemical sensitive membrane systems may then be applied to the windows of the devices to cover the gate regions.

5 Claims, 2 Drawing Figures

SYSTEM FOR ENCAPSULATION OF SEMICONDUCTOR CHIPS

BACKGROUND OF THE INVENTION

This invention relates to an encapsulation system for semiconductor chips where selected regions on the chip are exposed through the encapsulant.

For many uses of semiconductor devices, it is desired that the devices be encapsulated in some type of inert, protective coating both for protecting the device from the harmful effects of the environment in which the device may be used, which effects may lead to device degradation and failure, and for reducing the possibility that the device will contaminate the environment in which it is used. In a particular class of semiconductor devices sometimes referred to as chemical sensitive field-effect transistor transducers, it is necessary that certain regions on the devices remain exposed through windows or openings in encapsulant material. These devices, several embodiments of which are described in Johnson et al, U.S. Pat. No. 4,020,830, issued May 3, 1977, generally include a semiconductor substrate material, source and drain regions separated by a so-called gate region located at the surface of the substrate material, electrical insulator material overlying the source, drain and gate regions, and a chemical selective system overlying the insulator material above the gate region. The chemical selective system, which generally takes the form of a membrane, is adapted to interact with certain substances to which it is exposed and thereby modulate an electric field produced in the gate region. This modulation is dependent upon the chemical properties of the substances and thereby provides a measure of those chemical properties. Measurements which may be performed include measurement of ion activity, immunochemical concentrations, reducible gas concentrations, and concentrations of enzymes and substrates.

Because chemical sensitive devices are utilized specifically by exposing the devices to various substances and chemical solutions, it is necessary to cover (encapsulate) the entire surface area of the devices except for the chemical sensitive gate regions. Techniques heretofore used for encapsulating chemical sensitive devices include the simple hand dispensation of epoxy or other encapsulant on the device, leaving a window or opening over the gate region. The obvious problems with this technique are that it is time consuming and therefore costly, and difficult to maintain uniformity from one device to the next. Of course, the smaller the device, the more difficult it is to apply an encapsulant by hand and still leave an appropriate window over the gate region.

Another technique which has been considered for applying encapsulant to chemical sensitive devices involves deposition by hand, spinning, or other application technique of epoxy or other encapsulant over the entire surface area of a chip or wafer containing a plurality of devices. The encapsulant is then overlayed with a photoresist material, the material exposed to a predetermined light pattern, and the photoresist material developed. The encapsulant material is etched according to the exposure pattern to create windows over the gate regions of the devices in the chip or wafer. The problem with this technique is that the windows produced do not have vertical walls since the etchant tends to etch in the encapsulant material windows having generally V-shaped cross sections. It is desired that windows formed in encapsulant material have vertical walls to allow close packing of devices on a chip or wafer.

SUMMARY OF THE INVENTION

It is an object of the invention to provide a simple, inexpensive and efficient system for encapsulating semiconductor devices where one or more regions of the devices are to remain exposed through windows in the encapsulant.

It is another object of the invention to provide such a system which facilitates large-scale production of encapsulated semiconductor devices.

It is an additional object of the invention to provide an encapsulation system which yields uniform product results.

It is also an object of the invention to provide an encapsulation system wherein the windows or openings in the encapsulant material have generally vertical side walls.

The above and other objects of the invention are realized in a specific illustrative embodiment of a system for encapsulating at least a portion of a semiconductor wafer having a plurality of regions which are to be exposed through the encapsulant. This system includes lamination of one or more sheets of dry film photoresist material onto a surface of the wafer, alignment of a photomask with the wafer so that a predetermined light-transmitting pattern of the mask coincides with selected areas of the chip surface, directing light onto the photomask and through the light-transmitting pattern of the mask onto the wafer, and developing the photoresist material to remove material from over the regions which are to be exposed. Windows are thus defined in the photoresist material which serves as an encapsulant for the rest of the wafer.

The system of the present invention is especially advantageous for encapsulating chemical sensitive field-effect devices formed on a wafer. In such case, the windows are formed over the gate regions of the devices and then chemical sensitive membranes may be formed in the windows to adhere to the sides thereof. It has been found that typical membrane material, such as polyvinyl chloride matrices, adheres well to the sides of the windows formed in the photoresist material.

The above-described encapsulation system allows for the efficient production of encapsulated semiconductor devices having uniform size openings in the encapsulant at preselected locations. The devices thus produced are of high quality and have fairly uniform operating characteristics.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
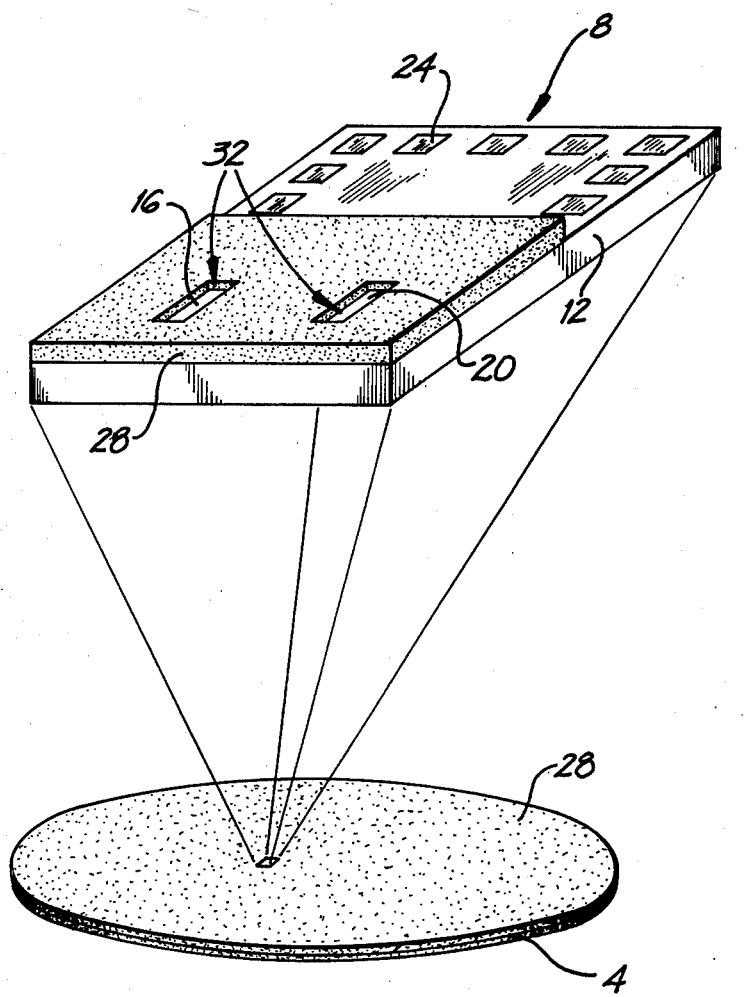
FIG. 1 is a perspective view of a semiconductor wafer whose surface has been encapsulated in accordance with the principles of the present invention, a portion of which wafer is shown magnified.

There is shown in FIG. 1 a silicon wafer 4 having formed therein a plurality of semiconductor chips or devices, one of which 8 is shown in magnified form. The wafer 4 is constructed using conventional semiconductor techniques to contain a large number of semiconductor chips, for example, from 200 to 2000 depending upon the size of the wafer and size of the chips. After such wafers are produced, they are cut or diced to separate the individual chips.

The semiconductor chip 8 shown in FIG. 1 includes a substrate 12 which is typically silicon, and a pair of field-effect transistor gate regions 16 and 20. Thus, the chip 8 carries two separate semiconductor devices, each having a gate region utilized by the device for detecting chemical properties of substances to which the device is exposed. Formed on the substrate 12 are a plurality of bonding pads 24 by which each of the devices may be connected to exterior circuitry. The construction and operation of the described semiconductor devices can be understood from the aforecited Johnson et al patent.

In accordance with a preferred embodiment of the present invention, one or more sheets of dry film photoresist material 28 is placed over the wafer 4 and laminated onto the wafer by a pressure and heating process. Suitable dry film photoresist sheets are available from Du Pont under the brand name "Riston". The sheets have a thickness of 50 microns, and for the embodiment of FIG. 1, two such sheets are laminated together onto the wafer 4 by passing the wafer and sheets through a type of wringer having heated silicone rubber rollers. The pressure selected should be sufficient to press the sheets against the wafer without damaging the wafer.

After the dry film photoresist material 28 is laminated onto the wafer, a conventional photomask made of glass or other suitable material is placed over and aligned with the wafer. The photomask includes a light-transmitting pattern and this pattern is aligned with predetermined regions of the wafer as will be described momentarily. The photomask and wafer are then exposed to high intensity ultraviolet light so that the light passes through the light-transmitting pattern of the photomask onto the dry film photoresist layer 28. If the photoresist material is a negative type, then the light-transmitting pattern in the photomask allows light to strike the dry film photoresist layer 28 over all areas except those coinciding with gate regions, such as regions 16 and 20 of the chip 8, formed in the devices in the wafer (and except those containing the bonding pads 24). If the dry film photoresist material is a positive type, then the light-transmitting pattern of the photomask allows light to strike the layer 28 only at those areas coinciding with the gate regions formed in the semiconductor devices (and the regions containing bonding pads).

The wafer is then developed to etch away the photoresist material defined by the pattern in the photomask. If the dry film photoresist layer 28 is negative, then the developer solution will remove photoresist material which was not exposed to light, and if positive, the solution will remove those areas exposed to light. In either case, the light-transmitting pattern of the photomask is selected so that the photoresist material which overlays the gate regions (and bonding pad regions) of the semiconductor chips is removed. This yields windows or openings, such as windows 32, formed in the dry film photoresist layer 28 through which the gate regions of the devices are exposed. The dry film photoresist layer 28 "develops" so that the sides of the resultant windows are substantially vertical and this allows close packing of devices on a wafer.

It should be mentioned that after the photoresist material 28 is applied to the wafer 4, and developed, the wafer is diced and the bonding pad regions are encapsulated after desired electrical connections are made.

With the above-described system, the dry film photoresist material serves as the encapsulant, while also allowing precise formation of windows therein to expose areas of the underlying semiconductor devices. It has also been found that this material facilitates placement of chemical sensitive membrane systems in the windows over the gate regions subsequent to encapsulation. This is because the chemical sensitive membrane material typically used, such as highly plasticized polyvinyl chloride matrices adhere well to the sides of the windows in the dry film photoresist material. Thus, the windows formed in the photoresist material expose the desired regions of the semiconductor devices and function as a mold to receive the chemical sensitive membrane material. The membrane material may be applied to the windows by micro injection and then cured at room temperature to fix the membranes in place.

Figure 2:
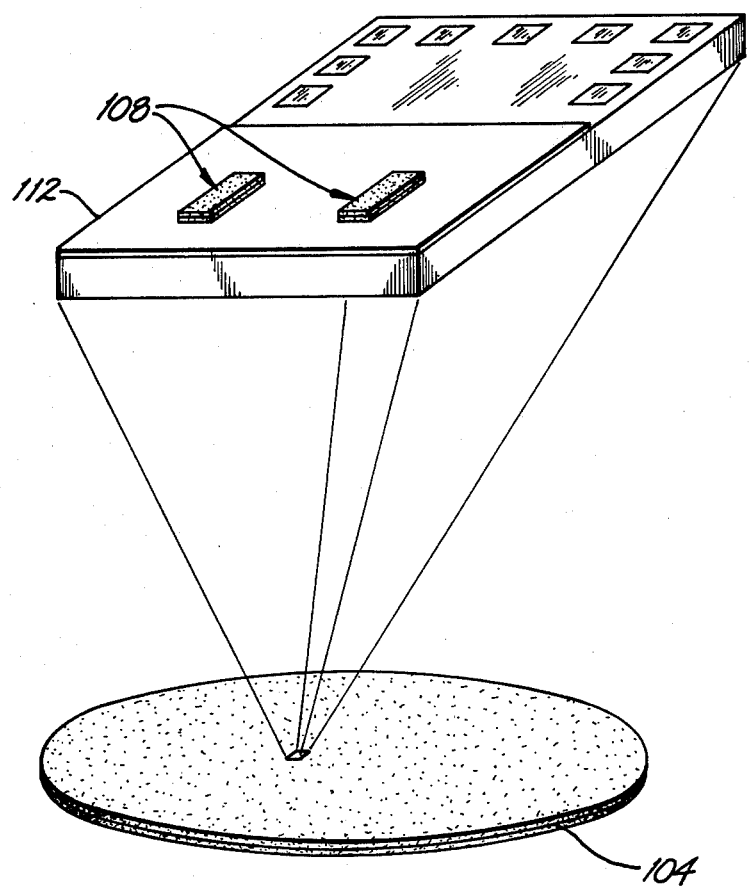
FIG. 2 is a perspective view of a semiconductor wafer whose surface has been encapsulated in accordance with an alternative embodiment of the invention, with a portion of this wafer also being magnified.

FIG. 2 shows an alternative encapsulation system for encapsulating semiconductor devices. With this system, the dry film photoresist layer is placed over a wafer 104 and then "developed", as described hereinbefore, to leave chimneys or pillars 108 formed over the gate regions of the chips. After this, the wafer is diced to obtain the individual semiconductor chips, desired electrical connections are made and then an encapsulant 112 is applied to each chip to cover the device portion thereof. Such encapsulant may be applied by hand to a thickness just less than the height of the pillars 108. Alternatively, the chips may be placed in wells and then flooded with the encapsulant material 112, again to a thickness just less than the height of the pillars. After the encapsulant material 112 has been applied to the chip, the pillars 108 are etched away to leave windows in the encapsulant.

One advantage of this alternative embodiment of an encapsulation system is greater flexibility in the choice of encapsulant material. Also, the gate regions are protected by the pillars 108 during handling and this helps to prevent contamination, damage, etc., to the gate regions.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A method of encapsulating at least a portion of a semiconductor wafer having a plurality of regions which are to be exposed through the encapsulant, said method comprising the steps of
    laminating one or more sheets of dry film photoresist material onto a surface of the wafer,
    aligning a photomask with the wafer so that a predetermined light-transmitting pattern of the mask coincides with certain areas of the wafer surface,
    directing light onto the photomask and through the light-transmitting pattern of the mask onto the wafer, and developing the photoresist material to remove the material from over said regions of the wafer to define windows in the material through which the regions are exposed, wherein the semiconductor wafer includes a plurality of field-effect transistor devices, each of which includes a gate region corresponding to a different one of the regions to be exposed through the encapsulant, said method further comprising the step of applying a chemical sensitive membrane system into each of the windows defined in the photoresist material to adhere to the sides of the windows and cover the corresponding exposed regions.

2. A method as in claim 1 wherein said laminating step includes placing the sheet of dry film photoresist material over the wafer, and passing the wafer and sheet of material through a pair of heated rollers so that the sheet is heated and pressed against the wafer.

3. A method as in claim 1 wherein said applying step comprises inserting the membrane systems into the windows by micro injection, and then curing the membrane systems in place.

4. A method of encapsulating semiconductor devices formed in a silicon wafer where each device includes a region which is to be exposed through the encapsulant, said method comprising the steps of laminating a sheet of dry film photoresist material onto a surface of the wafer, aligning a photomask with the wafer so that a preselected light-transmitting pattern of the mask is arranged in a certain predetermined relationship with respect to said regions, exposing the photomask to light so that the light passes through the light-transmitting pattern of the mask onto the wafer, washing the photoresist material with a developing solution to remove all materail from the wafer except for pillars of material located over said regions, applying an encapsulant to the surface of the wafer to cover all areas except those covered by the pillars of material, and washing the wafer with an etchant to remove the pillars of photoresist material to expose said regions.

5. A method as in claim 4 wherein said encapsulant applying step comprises dicing the wafer to obtain the individual and separate semiconductor devices, and electrically bonding the devices, and applying an encapsulant to cover areas of each device except that covered by the respective pillar of material.

* * * * *